(12) United States Patent
Ohrt et al.

(10) Patent No.: US 10,583,261 B2
(45) Date of Patent: Mar. 10, 2020

(54) INHALER

(71) Applicant: LIITA HOLDINGS LTD., Nicosia (CY)

(72) Inventors: Martin Ohrt, Frederiksberg (DK); Jeppe Paustian, Osterbro (DK); Søren Dyring Jensen, Valby (DK)

(73) Assignee: Liita Holdings LTD, Nicosia (CY)

( * ) Notice: Subject to any disclaimer, the term of this patent is extended or adjusted under 35 U.S.C. 154(b) by 747 days.

(21) Appl. No.: 14/904,426

(22) PCT Filed: Jul. 10, 2014

(86) PCT No.: PCT/EP2014/064799
§ 371 (c)(1),
(2) Date: Jan. 11, 2016

(87) PCT Pub. No.: WO2015/004227
PCT Pub. Date: Jan. 15, 2015

(65) Prior Publication Data
US 2016/0151589 A1    Jun. 2, 2016

(30) Foreign Application Priority Data

Jul. 12, 2013  (DK) .................................. 2013 70395

(51) Int. Cl.
*A61M 15/00* (2006.01)
*A61K 33/14* (2006.01)
(Continued)

(52) U.S. Cl.
CPC ....... *A61M 15/0065* (2013.01); *A61K 9/0075* (2013.01); *A61K 9/16* (2013.01);
(Continued)

(58) Field of Classification Search
CPC ...... A61M 15/00; A61M 15/0003–001; A61M 15/0021; A61M 15/0028; A61M 15/0033;
(Continued)

(56) References Cited

U.S. PATENT DOCUMENTS 5,161,524 A    11/1992  Evans
5,263,475 A *  11/1993  Altermatt .......... A61M 15/0065
                                                      128/203.15
(Continued)

FOREIGN PATENT DOCUMENTS

DE   10 2007 053590 A1   5/2009
EP        0211595 A2     2/1987
(Continued)

OTHER PUBLICATIONS

EP Appln. 14738492.9, communication to EPO dated Sep. 7, 2016.
(Continued)

*Primary Examiner* — Michael J Tsai
*Assistant Examiner* — Ned T Heffner
(74) *Attorney, Agent, or Firm* — Cheryl H Agris; Agris & von Natzmer, LLP

(57) ABSTRACT

Provided is an inhaler for halotherapy having in an axial direction a proximal end for insertion into the mouth of a user, and a distal end opposite to the proximal end, wherein the inhaler comprises an inlet, an outlet arranged at the proximal end, an air passage extending from the inlet to the outlet, and a reservoir communicating with the air passage through a release orifice, the reservoir containing a dispersible substance.

10 Claims, 2 Drawing Sheets

(51) Int. Cl.
*A61K 9/00* (2006.01)
*A61K 9/16* (2006.01)

(52) U.S. Cl.
CPC ......... *A61K 33/14* (2013.01); *A61M 15/0003* (2014.02); *A61M 15/0023* (2014.02); *A61M 15/0028* (2013.01); *A61M 15/0086* (2013.01); *A61M 15/0096* (2014.02); *A61M 2202/0468* (2013.01); *A61M 2202/064* (2013.01)

(58) Field of Classification Search
CPC ........... A61M 15/0035–0041; A61M 15/0043; A61M 15/0045; A61M 15/051; A61M 15/0065; A61M 15/0086; A61M 15/06; A61M 15/08–085; A61M 15/0023; A61J 1/10; A61J 1/14; A61J 1/20; A61J 1/2006–2017; A61K 9/14

See application file for complete search history.

(56) References Cited

U.S. PATENT DOCUMENTS

| | | | |
|---|---|---|---|
| 5,699,789 | A | 12/1997 | Hendricks |
| 2007/0062525 | A1* | 3/2007 | Bonney ............. A61M 15/0045 128/203.21 |
| 2009/0183744 | A1 | 7/2009 | Hayton |
| 2013/0092161 | A1 | 4/2013 | Von Schuckmann |
| 2013/0125888 | A1* | 5/2013 | Monterenzi ....... A61M 15/0065 128/203.15 |

FOREIGN PATENT DOCUMENTS

| | | |
|---|---|---|
| JP | H09 322938 A | 12/1997 |
| WO | 9309831 A1 | 5/1993 |
| WO | 9848875 A1 | 11/1998 |
| WO | 0121238 A2 | 3/2001 |
| WO | 2013076682 A | 5/2013 |

OTHER PUBLICATIONS

EP Appln. 14738492.9, communication from EPO dated Nov. 7, 2016.
PCT appln. No. PCT/EP2014/064799, International Preliminary Report on Patentability (IPRP) dated Dec. 1, 2016.
PCT appln. No. PCT/EP2014/064799, International Search Report, dated Oct. 13, 2014.
Danish Priority Appln. No. PA 2013 70395, Search Report from the Danish Patent Office, dated Feb. 13, 2014.
CN Appln. No. 2014839523, Response to Office Action (original and English translation), dated Oct. 19, 2018.
JP Appln. No. 20160524821, Response to Notification of Reasons for Refusal (original and English translation), dated Nov. 5, 2018.
CN Appln. No. 2014839523, Office Action (original and English translation), dated Jun. 4, 2018.
EP Appln. No. 14738492.9, communication to EPO dated May 17, 2017.
EP Appln. No. 14738492.9, communication from EPO (intention to grant a patent) dated Jul. 5, 2017.
JP Appln. No. 20160524821, Notification of Reasons for Refusal (original and English translation), dated May 30, 2018.
JP Appln. No. 20160524821, Search Report (original and English translation), dated May 25, 2018.
RU Appln. No. 2016104357/14 Search Report (original and English translation), dated Oct. 12, 2016.
RU Appln. No. 2016104357/14 1st Office Action (original and English translation).
RU Appln. No. 2016104357/14 Response to 1st Office Action (original and English translation).
Rashleigh et al. (2014) "A review of halotherapy for chronic obstructive pulmonary disease", Int. J COPD 9:239-246.
https://www.tecnosun.com/eng/grott.htm (wayback machine, dated Mar. 27 2010).
CN Appln. No. 2014839523, Intention to Grant Patent (Original and English Translation), dated Apr. 2, 2019.
CN Appln. No. 2014839523, Response to Second Office Action (Original and English Translation), dated Mar. 14, 2019.
CN Appln. No. 2014839523, Second Office Action (Original and English Translation), dated Jan. 30, 2019.
JP Appln. No. 20160524821, Claim Amendments (Original and English Translation), dated Jul. 26, 2019.
JP Appln. No. 20160524821, Written Opinion (Original and English Translation), dated Jul. 26, 2019.
JP Appln. No. 20160524821, Reasons for Refusal (Original and English Translation), dated Apr. 23, 2019.
RU Appln. No. 2016104357/14, Decision to Grant a Patent (Original and English Translation), dated Nov. 12, 2018.
MX Appln. No. MX/a/2016/000411, Official Action, dated Sep. 26, 2019 and commentary from agent dated Oct. 17, 2019.
IN Appln. No. 201617003751, Examination Report, dated Oct. 16, 2019.

* cited by examiner

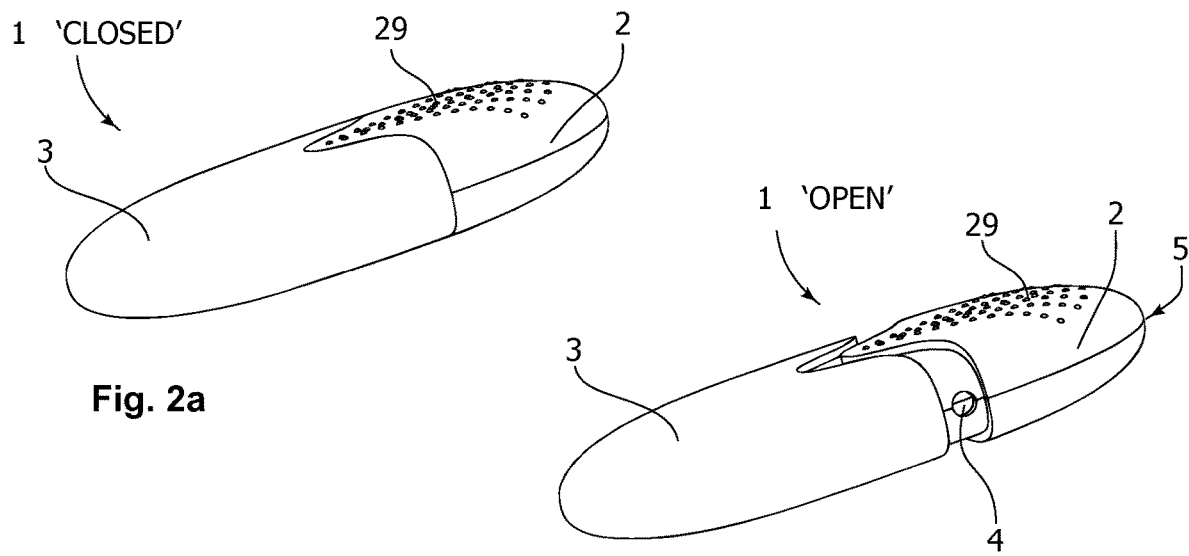
Fig. 2a
Fig. 2b
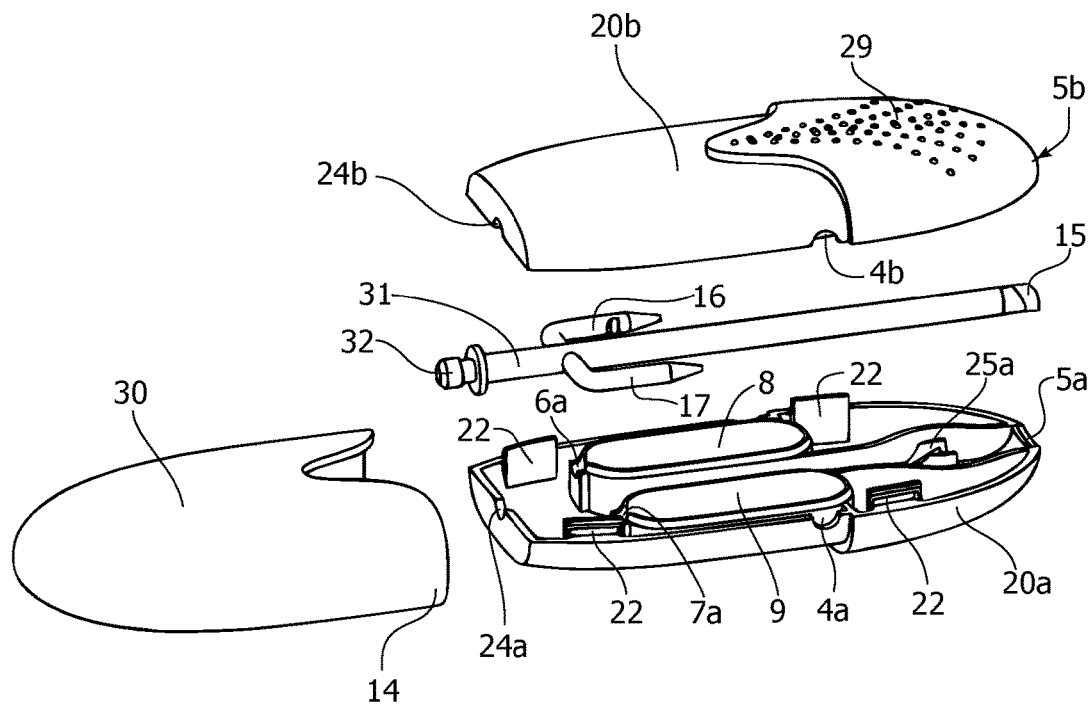
Fig. 3

INHALER

The invention relates to an inhaler having in an axial direction a proximal end for insertion into the mouth of a user, and a distal end opposite to the proximal end, wherein the inhaler comprises an inlet, an outlet arranged at the proximal end, an air passage extending from the inlet to the outlet, and a reservoir communicating with the air passage through a release orifice, the reservoir containing a dispersible substance. The user inhales the dispersible substance by breathing in through the air passage, wherein the dispersible substance is dispersed in the air stream to form an inhalable aerosol. In a particular aspect, the present invention relates to an inhaler for halotherapy.

BACKGROUND OF THE INVENTION

Halotherapy is a drug free treatment for relieving the symptoms and discomfort of respiratory conditions. As a core element, halotherapy includes inhalation of salt particles by a user, typically as an aerosol of micronized salt dispersed in air. While such a treatment may be applied without substantial complications and thus is suited for sale in an end-user/consumer market, a widespread use of such treatment is still hampered by the lack of cheaply available packages for user-friendly administration of halotherapy "on the go". Furthermore, acceptance of a product in and enduser/consumer market is usually highly sensitive to design and appearances. In the case of an inhaler, such a constraint dictated by the market means a technical construction that allows for an administration in an easy and discrete manner. Numerous inhalers for the administration of pharmaceutical drugs are known. However, all these inhalers are usually designed for precise dosing, are complex and costly to produce, and are cumbersome to use. Also a discrete use as might be desired for the administration in public spaces is usually not easily possible. Therefore, there is a need for a low-cost inhaler that is easy and discrete to use, and which is suited for commercialization on an end-user/consumer market.

SUMMARY OF THE INVENTION

The object is achieved by an inhaler according to claim 1. Advantageous embodiments are recited in the dependent claims and in the below description.

A first aspect of the invention relates to an inhaler, the inhaler having in an axial direction a proximal end for insertion into the mouth of a user, and a distal end opposite to the proximal end, wherein the inhaler comprises an inlet, an outlet arranged at the proximal end, an air passage extending from the inlet to the outlet, and a reservoir communicating with the air passage through a release orifice, the reservoir containing a dispersible substance, wherein the inhaler has a proximal part comprising the outlet, and a distal part attached to the proximal part, wherein the proximal part is slidable in the axial direction with respect to the distal part between an 'OPEN' position and a 'CLOSED' position, wherein the inhaler further comprises an inlet valve member, an outlet valve member, and a reservoir valve member, said inlet, outlet and reservoir valve members being arranged so as to simultaneously close the inlet, the outlet, and the release orifice when the proximal part is brought from the 'OPEN' position into the 'CLOSED' position, and to simultaneously open the inlet, open the outlet, and deliver an amount of the dispersible substance from the reservoir through the release orifice to the air passage when the proximal part is brought from the 'CLOSED' position into the 'OPEN' position.

The term 'dispersible substance' refers to a substance that is at least dispersible as particles in air so as to form an aerosol. The aerosol comprises a dispersed phase, the particles, wherein the dispersed phase is suspended in a continuous gas phase, which in the present case is air. The particles may be solid particles or droplets.

Preferably, the inhaler is in the 'OPEN' position when the proximal part is deployed from the distal part. In the deployed position, the proximal part and the distal part are shifted apart from each other. Further preferably, the inhaler is in the 'CLOSED' position when the proximal part is retracted towards the distal part. In the retracted position, the proximal part and the distal part are moved together. Most preferably, the proximal part is linearly slidable along the axial direction with respect to the distal part, i.e. the proximal part is deployed and retracted by a linear sliding movement along the axial direction.

The inhaler is shaped and dimensioned to be held by a user in one hand. Preferably, the inhaler has a size that fits into the hollow hand of a user. Preferably, the user holds the inhaler by gripping around the distal part, and with the thumb resting on the proximal part. The user may now deploy the proximal part by pushing the proximal part in the axial direction away from the distal part. When held in the above indicated manner, this movement is typically performed by the thumb pressing against the proximal part and in a direction away from the distal part. Once the proximal part is deployed, the inlet and the outlet are open, and thus the air passage through the inhaler is cleared. At the same time, an amount of the dispersible substance has been delivered to the air passage. By the simple movement of a thumb, the inhaler may thus be switched into the 'OPEN' position, where the air passage is unblocked and an amount of the dispersible substance is available in the air passage for inhalation. The inhaler is now in an activated state, and the user may set the proximal end of the inhaler with the outlet to the mouth and breath in, thereby sucking air through the air passage. The air stream entrains and disperses the amount of dispersible substance made available in the air passage, and an aerosol is formed, which is released through the outlet for inhaled administration to the user. After ended inhalation, the proximal portion is easily retracted into the distal part by a simple sliding movement along the axial direction, thereby bringing the proximal part into the 'CLOSED' position. When held in the above indicated manner, this movement may easily be performed by a simple movement of e.g. the thumb resting against the proximal part. In the 'CLOSED' position, all openings to the outside are closed, thereby protecting the inside of the inhaler including the air passage, the reservoir, the dosing mechanism, and the dispersible substance from contamination by the ingression of humidity, dust and/or dirt when e.g. transported in a pocket or a bag. Thereby, the inhaler is operable by a simple movement that can be performed by the user in a discrete way in a single handed operation.

Further according to one embodiment of the inhaler, the reservoir is arranged in the proximal part. In use, the distal part is typically held fixed in the hand of the user, while the proximal part is moved. By placing the reservoirs in the proximal part, the reservoirs are automatically agitated as a consequence of the operation of the inhaler, e.g. when deploying the proximal part. The dispersible substance is thereby agitated, thereby improving the delivery/transfer of the dispersible substance from the reservoir through the release orifice into the air passage. This is an advantage in particular when the dispersible substance is in the form of a powder of solid particles that otherwise might tend to clog together. Otherwise, clogging may impede proper transfer from the substance store in the reservoir to the air passage, and may further impede proper dispersion in air to form an inhalable aerosol suited to reach the intended target regions in the lung of the user.

Advantageously according to one embodiment of the invention, both the inlet and the outlet are arranged in the proximal part.

Further according to one embodiment of the inhaler, the inlet comprises one or more openings in a peripheral housing wall of the proximal part, the one or more openings facing radially outward, away from the axial direction, and the inlet valve member is formed by a peripheral housing wall of the distal part covering the openings when the proximal part is in the 'CLOSED' position. By enclosing the inlet openings in the 'CLOSED' position by a peripheral wall, an improved protection of the inlet during transport or storage is achieved, thereby improving the hygiene around the product. The sideways location with the inlet openings facing radially outward and away from the axial direction implies at least one change of direction of the air stream. This may provide an impingement deflector/baffle collecting solid or liquid particulate contaminants from the incoming air stream. Furthermore, changes in direction create turbulence improving the dispersion of the dispersible substance. Consequently, this embodiment may improve aerosol formation/quality.

Further according to one embodiment of the inhaler, the outlet comprises an axially oriented aperture and the outlet valve member is a plug attached to the distal part via an axially extending stem, the plug blocking the outlet when the proximal part is in the 'CLOSED' position. Placing the outlet valve at the proximal end of the inhaler as seen in the axial direction facilitates an easy operation of the inhaler.

Further according to one embodiment of the inhaler, the distal part comprises a central shaft extending along the axial direction from the outlet valve member at the proximal end to the distal end, wherein the central shaft is linked to the proximal part by a linear sliding bearing for movement along the axial direction. The central shaft provides a "backbone" for the construction, thereby stiffening the construction and improving the reliability of the linear sliding linkage between the proximal part and the distal part.

Preferably according to one embodiment, the central shaft carries the outlet valve member, and on side branches, the reservoir valve members. Thereby a simple and rugged construction is provided for the simultaneous operation of the outlet and reservoir valves. The outlet valve is formed by the outlet valve member cooperating with the outlet for controlling the flow of air/aerosol through the outlet. The reservoir valve is formed by the reservoir valve member cooperating with the release orifice for controlling the delivery/transfer of dispersible substance from the reservoir to the air passage.

Advantageously according to one embodiment, a mechanical end stop limiting the travel/excursion of the proximal part with respect to the distal part is provided. In one embodiment, the mechanical stop is provided by side branches of the central shaft of the distal part cooperating with a retaining element on the proximal part.

Advantageously according to one embodiment the distal part and the proximal part have cooperating locking means for engaging each other in the CLOSED position, such as but not limited to a latch, a spring-loaded catch, a peripherally located protrusion/rim cooperating with a dimple/groove to secure the proximal part in the retracted position where the inhaler is 'CLOSED'.

Further according to one embodiment of the inhaler, the release orifice is oriented in the axial direction and the reservoir valve member is a peg travelling in the axial direction, the peg being fixed to the distal part via an axially extending stem, wherein the peg blocks the release orifice when the proximal part is in the 'CLOSED' position. Thereby a simple design for a reservoir valve is achieved that may be operated simultaneously with the inlet and outlet valves by a single linear movement. Note also, that a typical orientation of the inhaler in use is with the outlet at the proximal end pointing in an upward direction, i.e. the proximal end is located higher than the distal end with respect to gravity. Therefore, placing the reservoir in the proximal part in this embodiment implies that the release orifices point downward (with respect to gravity). This is advantageous, in particular when the dispersible substance is a solid powder that usually trickles downward and thus accumulates at the bottom of the reservoir as seen with respect to gravity.

Further according to one embodiment of the inhaler, the peg is shaped as a dosing needle with a first sealing zone, a recess zone defining a dosing volume, and a second sealing zone, wherein in the first sealing zone blocks the release orifice and the recess zone communicates with the reservoir when the proximal part is in the 'CLOSED' position, and wherein the second sealing zone blocks the release orifice and the recess zone communicates with the air passage when the proximal part is in the 'OPEN' position. The reservoir valve member is shaped and dimensioned to seal the release orifice both in the 'OPEN' position and in the 'CLOSED' position. The reservoir valve member is further provided with a dosing recess defining a dosing volume. The dosing volume is located inside the reservoir, when the proximal portion is retracted, and is located in the air passage when the proximal portion deployed. Accordingly, the dosing volume moves from the inside of the reservoir through the release orifice to the air passage, when the proximal portion is moved from the 'CLOSED' position to the 'OPEN' position. During the travel, the dosing volume only communicates with either the inside of the reservoir or with the air passage, but not with both, thereby providing a transfer lock maintaining the store of dispersible substance in the reservoir sealed from the environment to avoid contamination, while transferring a defined amount of the dispersible substance to the air passage for dispersion in a stream of air.

Further according to one embodiment of the inhaler, the proximal part comprises a further reservoir with a further release orifice, the further reservoir comprising a further dispersible substance, and wherein the distal part comprises a further reservoir valve member, said further reservoir valve member being arranged so as to close the further release orifice when the proximal part is brought from the 'OPEN' position into the 'CLOSED' position, and to deliver an amount of the further dispersible substance from the further reservoir through the further release orifice to the air passage when the proximal part is brought from the 'CLOSED' position into the 'OPEN' position. By providing an additional reservoir a number of advantages are achieved. Firstly, an improved aerosol formation is achieved by providing the dispersible substance at two places and from separate delivery mechanisms into the air stream. This advantage is further enhanced by producing a counter stream of two air streams, each entraining an amount of dispersible substance from a different location in the air passage. For example, a first branch of the air passage may lead from a first opening of the inlet to a common mixing chamber in communication with a first reservoir, and a second branch of the air passage may lead from a second opening of the inlet to the common mixing chamber in communication with a second reservoir. The air passage may thus be adapted such that the air streams from the two branches meet each other in counter flow in the common mixing chamber where the dispersible substance from the two reservoirs is provided. The counter-flow air stream enhances turbulence and thus enhances mixing and dispersion of the dispersible substance in the air, thereby improving aerosol formation prior to reaching the user.

Advantageously according to one embodiment, an inhaler may be assembled from four parts. Preferably, the four parts are from a moulded material, such as injection moulded plastics.

Advantageously according to one embodiment the dispersible substance in the reservoir and the further dispersible substance in the further reservoir are the same. In addition to the above-mentioned advantages of improved aerosol formation, the reliability of the inhaler is improved by providing two separate reservoirs with the same dispersible substance. In case there is a failure in one of the reservoirs or associated dispensing mechanics, there is still delivery from the other reservoir.

Alternatively according to a further embodiment the dispersible substance in the reservoir and the further dispersible substance in the further reservoir are different. This is advantageous when different dispersible substances are to be administered in combination, but providing a mixture of the different dispersible substances in the one or more reservoirs is not desirable or even not possible, for instance due to chemical reactions that may occur between the two different dispersible substances when stored/mixed together prior to administration, or due to a tendency of the different dispersible substances to separate from a mixture. By storing the different substances in separate reservoirs and only mixing them in the air stream the combined administration of the different substances in one combined aerosol is facilitated and/or the shelf-life of the inhaler package for combination treatment is enhanced. Furthermore, an improved/controlled mixing at a controlled mixing ratio of the different dispersible substances is achieved.

Advantageously according to one embodiment, the dispersible substance is a powder of solid particles.

Further according to one embodiment of the inhaler, the dispersible substance is a salt suited for halotherapy, preferably a micronized salt, most preferably micronized NaCl. Micronized sodium chloride is a known active substance suited for halotherapy. The inhaler according to any of the above-mentioned embodiments both stores the micronized salt in a protected transportable package, directly available for inhalation essentially anywhere in a low-cost and user-friendly package. The inhaler according to any of the above-mentioned embodiments is therefore particularly well-suited for retail distribution of micronized salt for inhaled administration/halotherapy in an end-user/consumer market.

Further according to one embodiment of the inhaler, the dispersible substance is a powder of solid particles with a particle size in the range between 1 μm and 10 μm, preferably between 1 μm and 5 μm. A particle size of about 1 μm-5 μm is targeted for the reaching the pulmonary alveoli, whereas particle sizes above 5 μm typically target the upper portions of the respiratory tract.

According to a further aspect of the present invention, the dispersible substance is a volatile liquid. The volatile liquid may be retained in the reservoir, e.g. by capillary forces in a fibrous matrix or in an adsorptive material allowing for evaporation of the volatile liquid from the surface.

In this embodiment, the dispersible substance may be transferred by merely unblocking the release orifice, e.g. by fully retracting the reservoir valve members when the proximal portion is deployed, for allowing vapours of the volatile liquid to reach the air passage and to be dispersed in air to form an inhalable aerosol.

Advantageously according to one embodiment the volatile liquid is an essential oil.

For an inhaler with plural reservoirs it may be conceived that both a dispersible substance and a further, different dispersible substance may be a volatile liquid. However, caution is to be applied not to combine substances that prevent each other from being properly dispersed in air, such as due to lumping of a say hygroscopic powder when combined with a further dispersible substance in liquid form.

BRIEF DESCRIPTION OF THE DRAWINGS

In the following, the invention will be described in more detail with reference to the appended drawings, which show in FIG. 1 a cross-sectional top view of an inhaler according to one embodiment in the 'CLOSED' position (FIG. 1a) and in the 'OPEN' position (FIG. 1b), FIG. 2 a perspective side view of the inhaler of FIG. 1 in the 'CLOSED' position (FIG. 2a) and in the 'OPEN' position (FIG. 2b), and in FIG. 3 an exploded view of the inhaler of FIG. 1.

DETAILED DESCRIPTION OF PREFERRED EMBODIMENTS

Figure 1A:
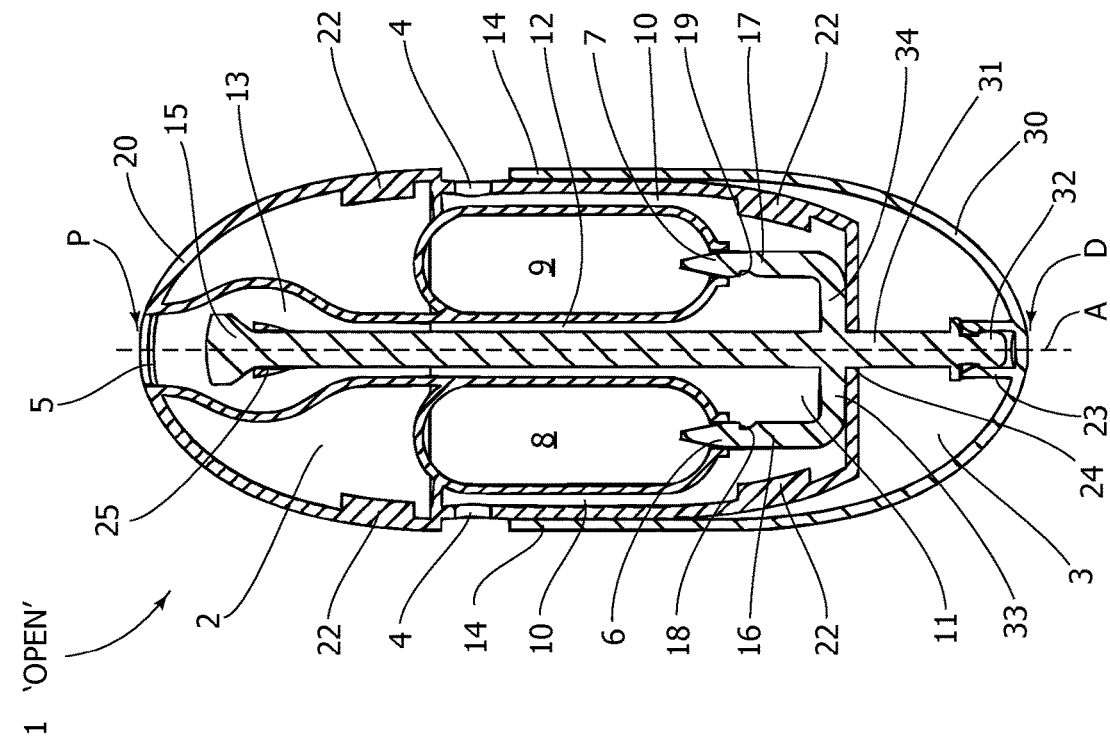
Figure 1B:
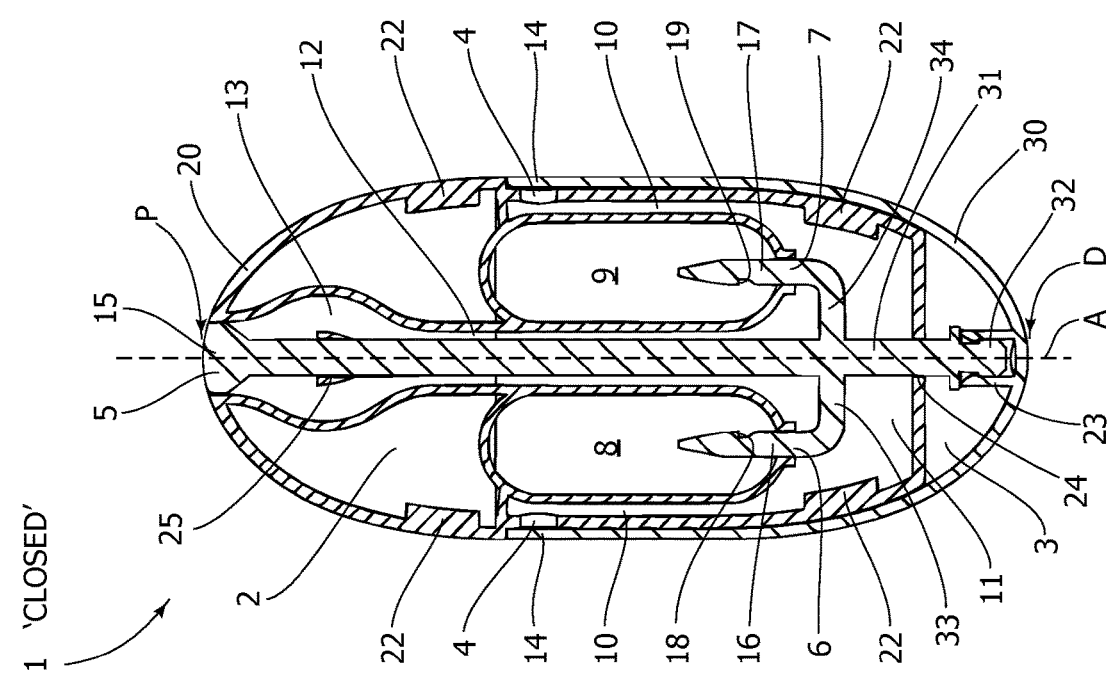

FIGS. 1a and 1b show an inhaler 1 for the inhalation of a solid powder according to one embodiment. The inhaler 1 has a proximal part 2 and a distal part 3. The proximal part 2 is displaceable with respect to the distal part 3 along an axial direction (broken line A) and can be shifted between a 'CLOSED' position where the proximal part 2 is retracted as shown in FIG. 1a, and an 'OPEN' position where the proximal part is deployed as shown in FIG. 1b.

The proximal part 2 has a housing portion 20 with two inlets 4 located on the side facing radially outward and away from the central axis A, an outlet 5 located at a proximal end P of the inhaler, and an air passage 10, 11, 12, 13 extending from the inlet 4 to the outlet 5. The proximal part 2 further comprises two reservoirs 8, 9 with a dispersible substance therein, that may be transferred from the reservoirs 8, 9 through respective release orifices 6, 7 into a common mixing chamber 11 in the air passage. The release orifices 6, 7 are arranged in the separation wall that defines the reservoirs 8, 9, in particular in portions thereof that face in an axial direction towards the distal end D of the inhaler 1. Besides the mixing chamber 11, the air passage comprises an upstream section 10 connecting the inlet 4 to the mixing chamber 11, and a downstream channel 12, 13, along the axial direction A, connecting the mixing chamber 11 to the outlet 5. A user inhales by putting the mouth to the outlet and breathing in. Driven by the suction of the user, air enters the inhaler 1 at the inlet 4 and flows from the inlet 4 via upstream section 10, to the mixing chamber 11; in the mixing chamber 11, an amount of the dispersible substance is added to the air stream, and due to turbulence occurring/generated in the mixing chamber dispersed and mixed into to the air stream to form an aerosol. The aerosol further follows the direction of the air stream from the mixing chamber 11 through the downstream channel sections 12, 13 to the outlet 5 from where it enters the mouth and finally reaches the lungs of the user.

The distal part 3 has a housing portion 30 in which the proximal part 2 is partially received, wherein the housing portion 30 of the distal part 3 has peripheral wall sections 14 that cover the inlets 4 when the proximal part 2 is retracted, and uncover the inlets 4 when the proximal part 2 is deployed. The wall sections 14 thus form inlet valve members that cooperate with the inlets 4 to block or unblock the intake of air into the air passage 10. The distal part 3 further comprises a central shaft 31 extending from the distal end D to the proximal end P of the inhaler 1. At the distal end D, the central shaft 31 is fixed to the inside of housing portion 30 by suitable attachment means 32, e.g. by gluing, or by a snap fit engagement facilitating easy assembly. At the proximal end P, a valve stem section of the central shaft 31 carries an outlet valve member 15. The outlet valve member 15 is a plug with a slightly conical shape that wedges into the opening of the outlet 5 from the inside when the proximal part 2 is retracted into the distal part 3 of the inhaler 1, thereby blocking the outlet 5. The central shaft 31 further carries side branches 33, 34 with reservoir valve members 16, 17 shaped as pegs in extension of axially extending stem sections at the outer end of the side branches 33, 34. The pegs are shaped and dimensioned to seal the release orifices 6, 7 both in the 'OPEN' position and in the 'CLOSED' position. The pegs are further provided with dosing recesses 18, 19 each defining a dosing volume. The dosing volume 18 is located inside the reservoir 8, when the proximal portion 2 is in the 'CLOSED' position, and is located in the mixing chamber 11 when the proximal portion 2 is in the 'OPEN' position. Accordingly, the dosing volume 19 moves from the inside of the reservoir 9 through the orifice 7 to the mixing chamber 11, when the proximal portion is deployed from the 'CLOSED' position to the 'OPEN' position. During the travel, the dosing volumes 18, 19 only communicate with either the inside of the respective reservoirs 8, 9 or with the mixing chamber 11, but not with both, thereby providing a transfer lock maintaining the store of dispersible substance in the reservoirs 8, 9 sealed from the environment to avoid contamination, while transferring a defined amount of the dispersible substance to the mixing chamber 11 for dispersion in a stream of air. The incoming air stream may contain droplets of humidity. To avoid lumping of a powdery substance to be dispersed, in the shown embodiment, the recess forming the dosing volume faces away from the incoming air-stream. Thereby, the risk of droplet deposition in the dosing volume, and thus the risk of lumping are largely reduced.

The proximal part 2 and the distal part 3 are linked together by a linear sliding bearing with bearings 24, 25 embracing distal and proximal sections of the axially extending central shaft 31. Further sliding bearings may be provided by the peg-shaped reservoir valve members 16, 17 sliding in an axial direction in the release orifices 6, 7. Radially extending portions of the side branches 33, 34 may provide a travel stop limiting excursion of the proximal part 2 during deployment. By some or all of these measures, a particularly stiff and rugged design of the inhaler is achieved in a simple construction facilitating low-cost production including assembly.

FIG. 2 shows a perspective side elevation view of the inhaler of FIG. 1 in the 'CLOSED' position (FIG. 2a) and in the 'OPEN' position (FIG. 2b). The inhaler 1 is intended to be held by a user (not shown) in the hollow hand, gripping around the distal part 3, and with the thumb resting on the proximal part 2. Advantageously, the proximal part 2 comprises friction/gripping means 29 on its outer surface. With the thumb set against these friction/gripping means 29, the user may now deploy the proximal part 2 by pushing the proximal part 2 in a direction away from the distal part 3. Suitable friction/gripping means 29 may be e.g. dimples, protrusions, a friction material applied to the outer surface of the housing portion of the proximal part, indentations, ripples or a combination thereof. When the proximal part 2 is deployed, the inlet 4 on the side is revealed, the outlet 5 is opened, and thus the air passage 10, 11, 12, 13 is cleared. In the 'CLOSED' position, all openings 4, 5 to the outside are closed, thereby protecting the inside of the inhaler 1 from the ingression of dust and dirt when e.g. transported in a pocket or bag. By the simple movement of a thumb, the inhaler 1 is switched into the 'OPEN' position, where inlet 4 and outlet 5 have been opened simultaneously, and at the same time an amount of the dispersible substance has been delivered to the mixing chamber 11 of the air passage. The inhaler 1 is now in an activated state, and the user may set the proximal end P of the inhaler 1 with the outlet 5 to the mouth and breath in, thereby sucking air through the air passage. The air stream entrains and disperses the amount of dispersible substance made available in the mixing chamber 11, and an aerosol is formed, which is released through the outlet 5 for inhaled administration to the user. In a typical position during such use, the proximal end P of the inhaler 1 will point in an upward direction, and consequently the release orifices 6, 7 inside the inhaler will point in a downward direction (with respect to gravity) thereby enhancing/facilitating the delivery of the powdery substance. Furthermore, by holding the distal part 3 and sliding the proximal part 2 containing the reservoirs 8, 9, the powdery substance inside the reservoirs 8, 9 is agitated without further means, thereby further enhancing the delivery of the dispersible substance in a simple and low-cost construction.

FIG. 3 shows an exploded view of an assembly of an inhaler according to the embodiment described above. In that assembly the inhaler has four parts that may be produced by a moulding technique, such as injection moulding. The distal part 3 has a single piece housing portion, and a central shaft 31 with an outlet valve member 15 at one end, and attachment means 32 at the opposite end. The central shaft 31 has side branches 33, 34 carrying reservoir valve members 16, 17 as described above. The central shaft 31 attaches to the inside of the outer housing portion 30 by a snap-fit engagement with the attachment means 32. The proximal part 2 is formed by two half-shells 20a, 20b that are attached to each other by a snap lock engagement of projections 22 on the bottom half-shell 20a engaging cooperating fastening means (not visible) on the inside of the top half-shell 20b, wherein the central shaft 31 is sandwiched between the two half-shells 20a, 20b. Once assembled, the central shaft 31 is embraced by sliding bearings with corresponding half-shells 24a/b, 25a/b. Thereby a simple assembly suited for low-cost high volume production is achieved. The proximal part further comprises reservoir sidewalls provided in the bottom half-shell 20a and cooperating reservoir sealing elements provided in the top half shell 20b. The reservoir sidewalls engage each other upon assembly of the two half-shells 20a, 20b to provide sealed reservoirs 8, 9. Prior to sealing the reservoirs by assembly of the two half-shells 20a, 20b, the reservoirs are filled with a dispersible substance, such as micronized salt. The sealed reservoirs 8,9 are only penetrated by release orifices 6, 7, which embrace the axially oriented peg-shaped reservoir valve members 16, 17. The reservoir valve members 16, 17 cooperate with the release orifices to control transfer of dispersible substance from the reservoirs 8, 9 to the common mixing chamber 11 of the air passage 10, 11, 12, 13.

REFERENCE NUMERALS 1 inhaler
2 proximal part
3 distal part
4 inlet
5 outlet
6, 7 release orifice
8, 9 reservoir
10, 11, 12, 13 air passage
14, 15, 16, 17 valve member
18, 19 dosing volume
20 housing
22, 23 engagement means
24, 25 linear sliding bearing
29 friction/gripping means
30 housing
31 central shaft
32 engagement means
33, 34 side branches
A longitudinal central axis along axial direction
D distal end
P proximal end

The invention claimed is:

1. An inhaler (1) having in an axial direction and in a linear configuration, a proximal end (P) for insertion into the mouth of a user, and a distal end (D) linearly opposite from the proximal end (P), wherein the inhaler (1) comprises an inlet (4), an outlet (5) for insertion into said user's mouth arranged at the proximal end (P), an air passage (10, 11, 12, 13) extending from the inlet (4) to the outlet (5), and a reservoir (8, 9) communicating with the air passage (10, 11, 12, 13) through a release orifice (6, 7), the reservoir (8, 9) containing a dispersible substance, wherein the inhaler (1) has a proximal part (2) comprising the outlet (5), and a distal part (3) attached to the proximal part (2), wherein the proximal part (2) is linearly slidable along the axial direction (A) with respect to the distal part (3) between an 'OPEN' position where the proximal part (2) is deployed from the distal part (3), and a 'CLOSED' position where the proximal part (2) is retracted towards the distal part (3), wherein the inhaler (1) further comprises a longitudinal central axis from said distal and proximal ends extending through said outlet, an inlet valve member (14), and an outlet valve member (15)
  wherein the reservoir (8, 9) is arranged in the proximal part (2);
  wherein the inlet (4) comprises one or more openings in a peripheral housing wall (20) of the proximal part (2), the one or more openings facing radially outward, away from axial direction (A), and the inlet valve member (14) is formed by a peripheral housing wall (30) of the distal part (3) covering the openings when the proximal part (2) is in the 'CLOSED' position;
  wherein the outlet (5) comprises an axially oriented aperture,
Characterized in that the outlet valve member (15) is formed as a plug attached to the distal part (3), the plug blocking the outlet (5) when the proximal part (2) is in the 'CLOSED' position;
  wherein the release orifice (6, 7) is oriented in the axial direction (A); and
  wherein the inhaler (1) further comprises a reservoir valve member (16, 17), wherein the reservoir valve member (16, 17) is formed as a peg travelling in the axial direction (A), the peg being fixed to the distal part (3) via an axially extended stem, wherein the peg blocks the release orifice (6,7) when the proximal part (2) is in the 'CLOSED' position; whereby said inlet valve member (14), outlet valve member (15) and reservoir valve member (16, 17) are arranged so as
  to simultaneously close the inlet (4), the outlet (5), and the release orifice (6, 7) when the proximal part (2) is retracted towards the distal part along the axial direction from the 'OPEN' position into the 'CLOSED' position, and
  to simultaneously open the inlet (4), open the outlet (5), and deliver an amount of the dispersible substance from the reservoir (8, 9) through the release orifice (6, 7) to the air passage (10, 11, 12, 13) when the proximal part (2) is linearly deployed from the distal part along the axial direction from the 'CLOSED' position into the 'OPEN' position.

2. The inhaler according to claim 1, wherein the peg is shaped as a dosing needle with a first sealing zone, a recess zone defining a dosing volume (18, 19), and a second sealing zone, wherein the first sealing zone blocks the release orifice (6, 7) and the recess zone communicates with the reservoir (8, 9) when the proximal part (2) is in the 'CLOSED' position, and wherein the second sealing zone blocks the release orifice (6, 7) and the recess zone communicates with the air passage (11) when the proximal part (2) is in the 'OPEN' position.

3. The inhaler according to claim 1, wherein the proximal part (2) comprises a further reservoir (9) with a further release orifice (7), the further reservoir (9) comprising a further dispersible substance, and wherein the distal part (3) comprises a further reservoir valve member (17), said further reservoir valve member (17) being arranged so as to close the further release orifice (7) when the proximal part (2) is brought from the 'OPEN' position with the particle size in the range between 1 μm and 5 μm into the 'CLOSED' position, and to deliver an amount of the further dispersible substance from the further reservoir (9) through the further release orifice (7) to the air passage (11) when the proximal part (2) is brought from the 'CLOSED' position into the 'OPEN' position.

4. The inhaler according to claim 1, wherein the dispersible substance is a salt suited for halotherapy.

5. The inhaler according to claim 1, wherein the dispersible substance is a powder of solid particles with a particle size in the range between 1 μm and 10 μm.

6. The inhaler according to claim 1, wherein the dispersible substance is a micronized salt.

7. The inhaler according to claim 1, wherein the dispersible substance is micronized NaCl.

8. The inhaler according to claim 1, wherein the dispersible substance is a powder of solid particles with a particle size in the range between 1 μm and 5 μm.

9. The inhaler according to claim 1, wherein the distal part (3) comprises a central shaft (31) extending along the axial direction (A) from the outlet valve member (15) at the proximal end (P) to the distal end (D), wherein the central shaft (31) is linearly linked to the proximal part (2) by a linear sliding bearing (24, 25) for movement along the axial direction (A).

10. The inhaler according to claim 9, wherein the central shaft (31) carries the outlet valve member (15), and on side branches, reservoir valve members (16, 17).

* * * * *